(12) United States Patent
Sutermeister et al.

(10) Patent No.: US 10,835,305 B2
(45) Date of Patent: Nov. 17, 2020

(54) RENAL NERVE MODULATION DEVICES AND METHODS

(71) Applicant: Boston Scientific Scimed, Inc., Maple Grove, MN (US)

(72) Inventors: Derek C. Sutermeister, Ham Lake, MN (US); Joel R. Munsinger, Blaine, MN (US); Timothy A Ostroot, Cokato, MN (US); James M. Anderson, Fridley, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 784 days.

(21) Appl. No.: 14/051,191

(22) Filed: Oct. 10, 2013

(65) Prior Publication Data
US 2014/0100562 A1 Apr. 10, 2014

Related U.S. Application Data

(60) Provisional application No. 61/712,138, filed on Oct. 10, 2012.

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1233* (2013.01); *A61B 18/1492* (2013.01);
(Continued)

(58) Field of Classification Search
CPC .......... A61B 2018/00755; A61B 2018/00875; A61B 18/1233; A61B 17/22004;
(Continued)

(56) References Cited

U.S. PATENT DOCUMENTS

| 164,184 A | 6/1875 | Kidder |
|---|---|---|
| 1,167,014 A | 1/1916 | O'Brien |

(Continued)

FOREIGN PATENT DOCUMENTS

| DE | 10038737 A1 | 2/2002 |
|---|---|---|
| EP | 1053720 A1 | 11/2000 |

(Continued)

OTHER PUBLICATIONS

US 8,398,630 B2, 03/2013, Demarais et al. (withdrawn)
(Continued)

*Primary Examiner* — Joseph A Stoklosa
*Assistant Examiner* — Tigist S Demie

(57) ABSTRACT

Systems for nerve and tissue modulation are disclosed. An example system may include an intravascular nerve modulation system including an elongated shaft having a proximal end region and a distal end region. The system may further include one or more ablation electrodes affixed to the distal end region of the elongated shaft. One or more ground pad electrodes may be provided and connected to a processor configured to modulate the impedance of each circuit completed between the ablation electrodes and the ground pads.

18 Claims, 3 Drawing Sheets

(51) Int. Cl.
- *A61B 18/00* (2006.01)
- *A61B 18/16* (2006.01)
- *A61B 17/22* (2006.01)
- *A61B 18/18* (2006.01)

(52) U.S. Cl.
CPC ......... *A61B 17/22004* (2013.01); *A61B 18/16* (2013.01); *A61B 18/1815* (2013.01); *A61B 2018/0022* (2013.01); *A61B 2018/00285* (2013.01); *A61B 2018/00404* (2013.01); *A61B 2018/00434* (2013.01); *A61B 2018/00577* (2013.01); *A61B 2018/00654* (2013.01); *A61B 2018/00755* (2013.01); *A61B 2018/00875* (2013.01); *A61B 2018/1467* (2013.01); *A61B 2018/165* (2013.01)

(58) Field of Classification Search
CPC ............ A61B 18/1206; A61B 18/1492; A61B 18/16; A61B 18/1815; A61B 2018/0022; A61B 2018/00285; A61B 2018/00404; A61B 2018/00434; A61B 2018/00577; A61B 2018/00654
See application file for complete search history.

(56) References Cited

U.S. PATENT DOCUMENTS

| | | | |
|---|---|---|---|
| 2,505,358 A | 4/1950 | Gusberg et al. | |
| 2,701,559 A | 2/1955 | Cooper | |
| 3,108,593 A | 10/1963 | Glassman | |
| 3,108,594 A | 10/1963 | Glassman | |
| 3,540,431 A | 11/1970 | Mobin | |
| 3,952,747 A | 4/1976 | Kimmell | |
| 3,996,938 A | 12/1976 | Clark, III | |
| 4,046,150 A | 9/1977 | Schwartz et al. | |
| 4,290,427 A | 9/1981 | Chin | |
| 4,402,686 A | 9/1983 | Medel | |
| 4,483,341 A | 11/1984 | Witteles et al. | |
| 4,574,804 A | 3/1986 | Kurwa | |
| 4,587,975 A | 5/1986 | Salo et al. | |
| 4,649,936 A | 3/1987 | Ungar et al. | |
| 4,682,596 A | 7/1987 | Bales et al. | |
| 4,709,698 A | 12/1987 | Johnston et al. | |
| 4,765,331 A | 8/1988 | Petruzzi et al. | |
| 4,770,653 A | 9/1988 | Shturman | |
| 4,784,132 A | 11/1988 | Fox et al. | |
| 4,784,162 A | 11/1988 | Ricks et al. | |
| 4,785,806 A | 11/1988 | Deckelbaum et al. | |
| 4,788,975 A | 12/1988 | Shturman et al. | |
| 4,790,310 A | 12/1988 | Ginsburg et al. | |
| 4,799,479 A | 1/1989 | Spears | |
| 4,823,791 A | 4/1989 | D'Amelio et al. | |
| 4,830,003 A | 5/1989 | Wolff et al. | |
| 4,849,484 A | 7/1989 | Heard | |
| 4,862,886 A | 9/1989 | Clarke et al. | |
| 4,887,605 A | 12/1989 | Angelsen et al. | |
| 4,920,979 A | 5/1990 | Bullara et al. | |
| 4,938,766 A | 7/1990 | Jarvik | |
| 4,955,377 A | 9/1990 | Lennox et al. | |
| 4,976,711 A | 12/1990 | Parins et al. | |
| 5,034,010 A | 7/1991 | Kittrell et al. | |
| 5,052,402 A | 10/1991 | Bencini et al. | |
| 5,053,033 A | 10/1991 | Clarke et al. | |
| 5,071,424 A | 12/1991 | Reger et al. | |
| 5,074,871 A | 12/1991 | Groshong et al. | |
| 5,098,429 A | 3/1992 | Sterzer et al. | |
| 5,098,431 A | 3/1992 | Rydell | |
| 5,109,859 A | 5/1992 | Jenkins | |
| 5,125,928 A | 6/1992 | Parins et al. | |
| 5,129,396 A | 7/1992 | Rosen et al. | |
| 5,139,496 A | 8/1992 | Hed | |
| 5,143,836 A | 9/1992 | Hartman et al. | |
| 5,156,610 A | 10/1992 | Reger et al. | |
| 5,158,564 A | 10/1992 | Schnepp-Pesch | |
| 5,170,802 A | 12/1992 | Mehra | |
| 5,178,620 A | 1/1993 | Eggers et al. | |
| 5,178,625 A | 1/1993 | Groshong et al. | |
| 5,190,540 A | 3/1993 | Lee | |
| 5,196,008 A * | 3/1993 | Kuenecke | A61B 18/16 606/32 |
| 5,211,651 A | 5/1993 | Reger et al. | |
| 5,234,407 A | 8/1993 | Teirstein et al. | |
| 5,242,441 A | 9/1993 | Avitall | |
| 5,251,634 A | 10/1993 | Weinberg et al. | |
| 5,255,679 A | 10/1993 | Imran | |
| 5,263,493 A | 11/1993 | Avitall | |
| 5,267,954 A | 12/1993 | Nita et al. | |
| 5,277,201 A | 1/1994 | Stern et al. | |
| 5,282,484 A | 2/1994 | Reger et al. | |
| 5,286,254 A | 2/1994 | Shapland et al. | |
| 5,295,484 A | 3/1994 | Marcus | |
| 5,297,564 A | 3/1994 | Love et al. | |
| 5,300,068 A | 4/1994 | Rosar et al. | |
| 5,301,683 A | 4/1994 | Durkan | |
| 5,304,115 A | 4/1994 | Pflueger et al. | |
| 5,304,121 A | 4/1994 | Sahatjian | |
| 5,304,171 A | 4/1994 | Gregory et al. | |
| 5,304,173 A | 4/1994 | Kittrell et al. | |
| 5,306,250 A | 4/1994 | March et al. | |
| 5,312,328 A | 5/1994 | Nita et al. | |
| 5,314,466 A | 5/1994 | Stern et al. | |
| 5,322,064 A | 6/1994 | Lundquist | |
| 5,324,255 A | 6/1994 | Passafaro et al. | |
| 5,326,341 A | 7/1994 | Lew et al. | |
| 5,326,342 A | 7/1994 | Pflueger et al. | |
| 5,330,518 A | 7/1994 | Neilson et al. | |
| 5,333,614 A | 8/1994 | Feiring | |
| 5,342,292 A | 8/1994 | Nita et al. | |
| 5,344,395 A | 9/1994 | Whalen et al. | |
| 5,364,392 A | 11/1994 | Warner et al. | |
| 5,365,172 A | 11/1994 | Hrovat et al. | |
| 5,368,557 A | 11/1994 | Nita et al. | |
| 5,368,558 A | 11/1994 | Nita et al. | |
| 5,380,274 A | 1/1995 | Nita et al. | |
| 5,380,319 A | 1/1995 | Saito et al. | |
| 5,382,228 A | 1/1995 | Nita et al. | |
| 5,383,874 A | 1/1995 | Jackson et al. | |
| 5,383,917 A | 1/1995 | Desai et al. | |
| 5,397,301 A | 3/1995 | Pflueger et al. | |
| 5,397,339 A | 3/1995 | Desai | |
| 5,401,272 A | 3/1995 | Perkins et al. | |
| 5,403,311 A | 4/1995 | Abele et al. | |
| 5,405,318 A | 4/1995 | Nita et al. | |
| 5,405,346 A | 4/1995 | Grundy et al. | |
| 5,409,000 A | 4/1995 | Imran | |
| 5,417,672 A | 5/1995 | Nita et al. | |
| 5,419,767 A | 5/1995 | Eggers et al. | |
| 5,427,118 A | 6/1995 | Nita et al. | |
| 5,432,876 A | 7/1995 | Appeldorn et al. | |
| 5,441,498 A | 8/1995 | Perkins et al. | |
| 5,447,509 A | 9/1995 | Mills et al. | |
| 5,451,207 A | 9/1995 | Yock et al. | |
| 5,453,091 A | 9/1995 | Taylor et al. | |
| 5,454,788 A | 10/1995 | Walker et al. | |
| 5,454,809 A | 10/1995 | Janssen | |
| 5,455,029 A | 10/1995 | Hartman et al. | |
| 5,456,682 A | 10/1995 | Edwards et al. | |
| 5,457,042 A | 10/1995 | Hartman et al. | |
| 5,471,982 A | 12/1995 | Edwards et al. | |
| 5,474,530 A | 12/1995 | Passafaro et al. | |
| 5,478,351 A | 12/1995 | Meade et al. | |
| 5,496,311 A | 3/1996 | Abele et al. | |
| 5,496,312 A | 3/1996 | Klicek et al. | |
| 5,498,261 A | 3/1996 | Strul | |
| 5,505,201 A | 4/1996 | Grill et al. | |
| 5,505,730 A | 4/1996 | Edwards | |
| 5,507,744 A | 4/1996 | Tay et al. | |
| 5,522,873 A | 6/1996 | Jackman et al. | |
| 5,531,520 A | 7/1996 | Grimson et al. | |
| 5,540,656 A | 7/1996 | Pflueger et al. | |
| 5,540,679 A | 7/1996 | Fram et al. | |
| 5,540,681 A | 7/1996 | Strul et al. | |
| 5,542,917 A | 8/1996 | Nita et al. | |

(56) References Cited

U.S. PATENT DOCUMENTS

| | | |
|---|---|---|
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker |
| 5,681,282 A | 10/1997 | Eggers et al. |
| RE35,656 E | 11/1997 | Feinberg |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh |
| 6,030,611 A | 2/2000 | Gorecki et al. |
| 6,032,675 A | 3/2000 | Rubinsky et al. |
| 6,033,397 A | 3/2000 | Laufer et al. |

(56) References Cited

U.S. PATENT DOCUMENTS

| | | |
|---|---|---|
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |

(56) References Cited

U.S. PATENT DOCUMENTS

| | | |
|---|---|---|
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |

(56) References Cited

U.S. PATENT DOCUMENTS

| | | | |
|---|---|---|---|
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,860,881 B2 * | 3/2005 | Sturm ............. A61B 18/1233 606/32 |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |

(56) References Cited

U.S. PATENT DOCUMENTS

| | | |
|---|---|---|
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Kr et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,566,322 B2 | 7/2009 | Jarrard et al. |
| 7,566,332 B2 * | 7/2009 | Jarrard ............... A61B 18/1233 606/32 |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |

(56) References Cited

U.S. PATENT DOCUMENTS

| | | |
|---|---|---|
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,883,507 B2 | 2/2011 | Jarrard et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,096,988 B2 | 1/2012 | Jarrard et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |

(56) References Cited

U.S. PATENT DOCUMENTS

| | | | |
|---|---|---|---|
| 8,486,063 B2 | 7/2013 | Werneth et al. | |
| 8,488,591 B2 | 7/2013 | Miali et al. | |
| 8,777,940 B2* | 7/2014 | Dunning | A61B 18/16 606/35 |
| 8,801,703 B2* | 8/2014 | Gregg | A61B 18/1233 606/32 |
| 9,066,720 B2* | 6/2015 | Ballakur | A61B 18/10 |
| 9,339,332 B2* | 5/2016 | Srivastava | A61B 17/320068 |
| 9,345,900 B2* | 5/2016 | Wu | A61B 18/1206 |
| 2001/0007070 A1 | 7/2001 | Stewart et al. | |
| 2001/0039419 A1 | 11/2001 | Francischelli et al. | |
| 2002/0022864 A1 | 2/2002 | Mahvi et al. | |
| 2002/0042639 A1 | 4/2002 | Murphy-Chutorian et al. | |
| 2002/0045811 A1 | 4/2002 | Kittrell et al. | |
| 2002/0045890 A1 | 4/2002 | Celliers et al. | |
| 2002/0062146 A1 | 5/2002 | Makower et al. | |
| 2002/0065542 A1 | 5/2002 | Lax et al. | |
| 2002/0087151 A1 | 7/2002 | Mody et al. | |
| 2002/0095197 A1 | 7/2002 | Lardo et al. | |
| 2002/0107536 A1 | 8/2002 | Hussein | |
| 2002/0147480 A1 | 10/2002 | Mamayek | |
| 2002/0169444 A1 | 11/2002 | Mest et al. | |
| 2002/0198520 A1 | 12/2002 | Coen et al. | |
| 2003/0045871 A1* | 3/2003 | Jain | A61B 18/1206 606/41 |
| 2003/0065317 A1 | 4/2003 | Rudie et al. | |
| 2003/0092995 A1 | 5/2003 | Thompson | |
| 2003/0139689 A1 | 7/2003 | Shturman et al. | |
| 2003/0195501 A1 | 10/2003 | Sherman et al. | |
| 2003/0199747 A1 | 10/2003 | Michlitsch et al. | |
| 2004/0010118 A1 | 1/2004 | Zerhusen et al. | |
| 2004/0019348 A1 | 1/2004 | Stevens et al. | |
| 2004/0024371 A1 | 2/2004 | Plicchi et al. | |
| 2004/0043030 A1 | 3/2004 | Griffiths et al. | |
| 2004/0064090 A1 | 4/2004 | Keren et al. | |
| 2004/0073206 A1 | 4/2004 | Foley et al. | |
| 2004/0088002 A1 | 5/2004 | Boyle et al. | |
| 2004/0093055 A1 | 5/2004 | Bartorelli et al. | |
| 2004/0106871 A1 | 6/2004 | Hunyor et al. | |
| 2004/0117032 A1 | 6/2004 | Roth | |
| 2004/0147915 A1 | 7/2004 | Hasebe | |
| 2004/0162555 A1 | 8/2004 | Farley et al. | |
| 2004/0167506 A1 | 8/2004 | Chen | |
| 2004/0186356 A1 | 9/2004 | O'Malley et al. | |
| 2004/0187875 A1 | 9/2004 | He et al. | |
| 2004/0193211 A1 | 9/2004 | Voegele et al. | |
| 2004/0220556 A1 | 11/2004 | Cooper et al. | |
| 2004/0243022 A1 | 12/2004 | Carney et al. | |
| 2004/0253304 A1 | 12/2004 | Gross et al. | |
| 2004/0267250 A1 | 12/2004 | Yon et al. | |
| 2005/0010095 A1 | 1/2005 | Stewart et al. | |
| 2005/0015125 A1 | 1/2005 | Mioduski et al. | |
| 2005/0080374 A1 | 4/2005 | Esch et al. | |
| 2005/0129616 A1 | 6/2005 | Salcedo et al. | |
| 2005/0137180 A1 | 6/2005 | Robinson et al. | |
| 2005/0143817 A1 | 6/2005 | Hunter et al. | |
| 2005/0148842 A1 | 7/2005 | Wang et al. | |
| 2005/0149069 A1 | 7/2005 | Bertolero et al. | |
| 2005/0149080 A1 | 7/2005 | Hunter et al. | |
| 2005/0149158 A1 | 7/2005 | Hunter et al. | |
| 2005/0149173 A1 | 7/2005 | Hunter et al. | |
| 2005/0149175 A1 | 7/2005 | Hunter et al. | |
| 2005/0154277 A1 | 7/2005 | Tang et al. | |
| 2005/0154445 A1 | 7/2005 | Hunter et al. | |
| 2005/0154453 A1 | 7/2005 | Hunter et al. | |
| 2005/0154454 A1 | 7/2005 | Hunter et al. | |
| 2005/0165389 A1 | 7/2005 | Swain et al. | |
| 2005/0165391 A1 | 7/2005 | Maguire et al. | |
| 2005/0165467 A1 | 7/2005 | Hunter et al. | |
| 2005/0165488 A1 | 7/2005 | Hunter et al. | |
| 2005/0175661 A1 | 8/2005 | Hunter et al. | |
| 2005/0175662 A1 | 8/2005 | Hunter et al. | |
| 2005/0175663 A1 | 8/2005 | Hunter et al. | |
| 2005/0177103 A1 | 8/2005 | Hunter et al. | |
| 2005/0177225 A1 | 8/2005 | Hunter et al. | |
| 2005/0181004 A1 | 8/2005 | Hunter et al. | |
| 2005/0181008 A1 | 8/2005 | Hunter et al. | |
| 2005/0181011 A1 | 8/2005 | Hunter et al. | |
| 2005/0181977 A1 | 8/2005 | Hunter et al. | |
| 2005/0182479 A1 | 8/2005 | Bonsignore et al. | |
| 2005/0183728 A1 | 8/2005 | Hunter et al. | |
| 2005/0186242 A1 | 8/2005 | Hunter et al. | |
| 2005/0186243 A1 | 8/2005 | Hunter et al. | |
| 2005/0191331 A1 | 9/2005 | Hunter et al. | |
| 2005/0203410 A1 | 9/2005 | Jenkins | |
| 2005/0209587 A1 | 9/2005 | Joye et al. | |
| 2005/0214205 A1 | 9/2005 | Salcedo et al. | |
| 2005/0214207 A1 | 9/2005 | Salcedo et al. | |
| 2005/0214208 A1 | 9/2005 | Salcedo et al. | |
| 2005/0214209 A1 | 9/2005 | Salcedo et al. | |
| 2005/0214210 A1 | 9/2005 | Salcedo et al. | |
| 2005/0214268 A1 | 9/2005 | Cavanagh et al. | |
| 2005/0228286 A1 | 10/2005 | Messerly et al. | |
| 2005/0228415 A1 | 10/2005 | Gertner | |
| 2005/0228460 A1 | 10/2005 | Levin et al. | |
| 2005/0232921 A1 | 10/2005 | Rosen et al. | |
| 2005/0234312 A1 | 10/2005 | Suzuki et al. | |
| 2005/0245862 A1 | 11/2005 | Seward | |
| 2005/0251116 A1 | 11/2005 | Steinke et al. | |
| 2005/0252553 A1 | 11/2005 | Ginggen | |
| 2005/0256398 A1 | 11/2005 | Hastings et al. | |
| 2005/0267556 A1 | 12/2005 | Shuros et al. | |
| 2005/0288730 A1* | 12/2005 | Deem | A61B 18/1492 607/42 |
| 2006/0004323 A1 | 1/2006 | Chang et al. | |
| 2006/0018949 A1 | 1/2006 | Ammon et al. | |
| 2006/0024564 A1 | 2/2006 | Manclaw | |
| 2006/0025765 A1 | 2/2006 | Landman et al. | |
| 2006/0062786 A1 | 3/2006 | Salcedo et al. | |
| 2006/0083194 A1 | 4/2006 | Dhrimaj et al. | |
| 2006/0089637 A1 | 4/2006 | Werneth et al. | |
| 2006/0089638 A1 | 4/2006 | Carmel et al. | |
| 2006/0095096 A1 | 5/2006 | DeBenedictis et al. | |
| 2006/0106375 A1 | 5/2006 | Werneth et al. | |
| 2006/0142790 A1 | 6/2006 | Gertner | |
| 2006/0147492 A1 | 7/2006 | Hunter et al. | |
| 2006/0167106 A1 | 7/2006 | Zhang et al. | |
| 2006/0167498 A1 | 7/2006 | DiLorenzo | |
| 2006/0171895 A1 | 8/2006 | Bucay-Couto | |
| 2006/0184221 A1 | 8/2006 | Stewart et al. | |
| 2006/0195139 A1 | 8/2006 | Gertner | |
| 2006/0206150 A1 | 9/2006 | Demarais et al. | |
| 2006/0224153 A1 | 10/2006 | Fischell et al. | |
| 2006/0239921 A1 | 10/2006 | Mangat et al. | |
| 2006/0240070 A1 | 10/2006 | Cromack et al. | |
| 2006/0247266 A1 | 11/2006 | Yamada et al. | |
| 2006/0247760 A1 | 11/2006 | Ganesan et al. | |
| 2006/0263393 A1 | 11/2006 | Demopulos et al. | |
| 2006/0265015 A1* | 11/2006 | Demarais | A61N 1/36007 607/2 |
| 2006/0269555 A1 | 11/2006 | Salcedo et al. | |
| 2006/0271111 A1 | 11/2006 | Demarais et al. | |
| 2006/0287644 A1 | 12/2006 | Inganas et al. | |
| 2007/0016184 A1 | 1/2007 | Cropper et al. | |
| 2007/0016274 A1 | 1/2007 | Boveja et al. | |
| 2007/0027390 A1 | 2/2007 | Maschke et al. | |
| 2007/0043077 A1 | 2/2007 | Mewshaw et al. | |
| 2007/0043409 A1 | 2/2007 | Brian et al. | |
| 2007/0049919 A1* | 3/2007 | Lee, Jr. | A61B 18/1233 606/34 |
| 2007/0049924 A1 | 3/2007 | Rahn | |
| 2007/0066972 A1 | 3/2007 | Ormsby et al. | |
| 2007/0073151 A1 | 3/2007 | Lee | |
| 2007/0093710 A1 | 4/2007 | Maschke | |
| 2007/0100405 A1 | 5/2007 | Thompson et al. | |
| 2007/0106247 A1 | 5/2007 | Burnett et al. | |
| 2007/0112327 A1 | 5/2007 | Yun et al. | |
| 2007/0118107 A1 | 5/2007 | Francischelli et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0149963 A1 | 6/2007 | Matsukuma et al. | |
| 2007/0162109 A1 | 7/2007 | Davila et al. | |
| 2007/0173805 A1 | 7/2007 | Weinberg et al. | |

(56) References Cited

U.S. PATENT DOCUMENTS

| | | |
|---|---|---|
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0051777 A1* | 2/2008 | Haemmerich ..... A61B 18/1233 606/33 |
| 2008/0064957 A1 | 3/2008 | Spence |
| 2008/0071269 A1 | 3/2008 | Hilario et al. |
| 2008/0071306 A1 | 3/2008 | Gertner |
| 2008/0082097 A1 | 4/2008 | McPherson |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0221565 A1* | 9/2008 | Eder ................. A61B 18/1206 606/40 |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036885 A1* | 2/2009 | Gregg ................. A61B 18/1233 606/35 |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |

(56) References Cited

U.S. PATENT DOCUMENTS

| | | |
|---|---|---|
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1* | 12/2011 | Wang ............... A61B 5/4893 600/301 |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0144251 A1* | 6/2013 | Sobotka ............. A61N 1/36053 604/500 |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1* | 7/2013 | Smith ............... A61B 18/1492 606/41 |
| 2013/0172879 A1 | 7/2013 | Sutermeister |
| 2013/0172880 A1 | 7/2013 | Willard |
| 2013/0172881 A1 | 7/2013 | Hill et al. |
| 2014/0018880 A1* | 1/2014 | Zarins ............... A61N 1/36117 607/44 |

(56) References Cited

U.S. PATENT DOCUMENTS

| | | | | |
|---|---|---|---|---|
| 2015/0080884 | A1* | 3/2015 | Zarins | A61B 18/1492 606/41 |
| 2015/0320481 | A1* | 11/2015 | Cosman, Jr. | A61B 19/5225 606/35 |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 2022428 A1 | 2/2009 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | 03026525 A1 | 4/2003 |
| WO | 2004100813 A2 | 11/2004 |
| WO | 2004110258 A2 | 12/2004 |
| WO | 2006105121 A2 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2011005901 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," Volcano Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, an Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.

(56) References Cited

OTHER PUBLICATIONS

Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Cryoanalgesia," Forefront Publishing Group, 1995, Neurological Research, vol. 17, August, p. 307-311.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.

\* cited by examiner

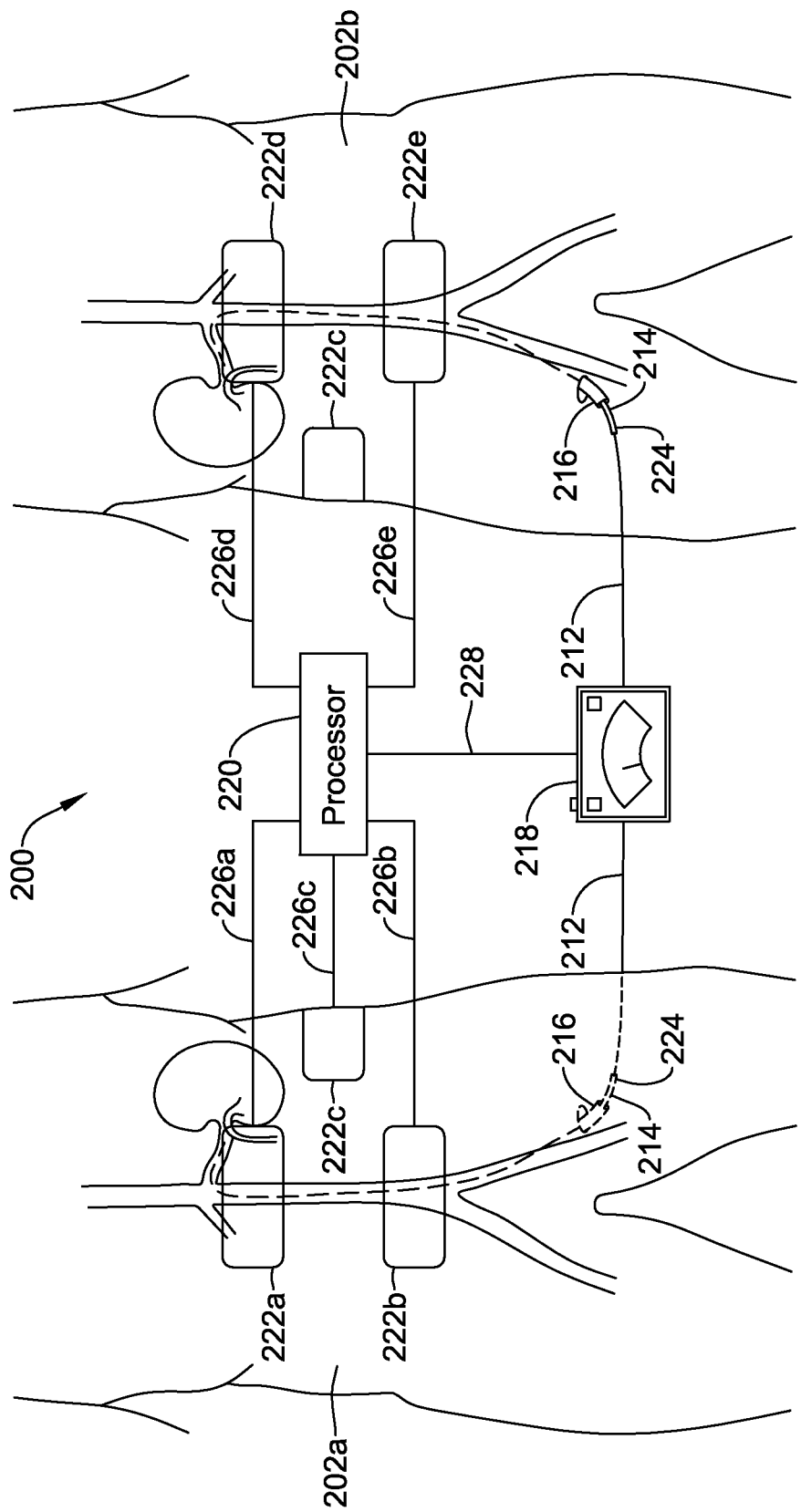

RENAL NERVE MODULATION DEVICES AND METHODS

CROSS-REFERENCE TO RELATED APPLICATIONS

This application claims priority under 35 U.S.C. § 119 to U.S. Provisional Application Ser. No. 61/712,138, filed Oct. 10, 2012, the entirety of which is incorporated herein by reference.

TECHNICAL FIELD

The present disclosure pertains to medical devices and methods for making and using medical devices. More particularly, the present disclosure pertains to medical devices and methods for performing renal nerve modulation.

BACKGROUND

Certain treatments require the temporary or permanent interruption or modification of select nerve function. One example treatment is renal nerve ablation, which is sometimes used to treat conditions related to congestive heart failure or hypertension. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many nerves, including renal nerves, run along the walls of or in close proximity to blood vessels and thus can be accessed via the blood vessels. In some instances, it may be desirable to ablate perivascular renal nerves using radiofrequency energy. In all circuits, completion of the circuit is made using the path of least resistance. In radiofrequency ablation circuits involving the body, the path of least resistance is often through muscle. Because muscle is of lower impedance than connective tissue, the propensity for generating inconsistent lesions may be greater if connective, fatty, and muscular tissues are all present. In a case such as this, the lesions generated may be of lesser or greater depth based upon tissue presence and type. Also, bowel or psoas muscle burns may occur. It may be desirable to provide for alternative systems and methods for reducing unintended lesions and for improving lesion consistency within variable anatomy.

SUMMARY

The disclosure is directed to several alternative designs, materials and use alternatives for medical device structures and assemblies. An example use may include a method for performing intravascular renal nerve modulation. The method may include providing a nerve modulation system including an elongate shaft having a proximal end region and a distal end region and one or more ablation electrodes positioned adjacent the distal end region of the elongate shaft. The system may also include two or more ground pads, a control unit electrically coupled to the one or more ablation electrodes, and a processor electrically coupled to the two or more ground pads. The modulation system may be advanced through a lumen such that the distal end region is adjacent to a target region. Voltage may then be applied to the one or more ablation electrodes, wherein energy flows between the one or more ablation electrodes and the two or more ground pads to form individual circuits. The resistance of at least one of the circuits formed between the ground pads and the ablation electrodes may also be adjusted.

An example medical device may include an intravascular nerve modulation system. The nerve modulation system may include an elongate shaft having a proximal end region and a distal end region and an ablation electrode positioned adjacent the distal end region of the elongate shaft. The system may also include at least two ground pads, a control unit electrically coupled to the one or more ablation electrodes, and a processor electrically coupled to the two or more ground pads.

The above summary of some example embodiments is not intended to describe each disclosed embodiment or every implementation of the invention. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which:

FIG. 3 is another schematic view illustrating a renal nerve modulation system in situ;

Figure 1:
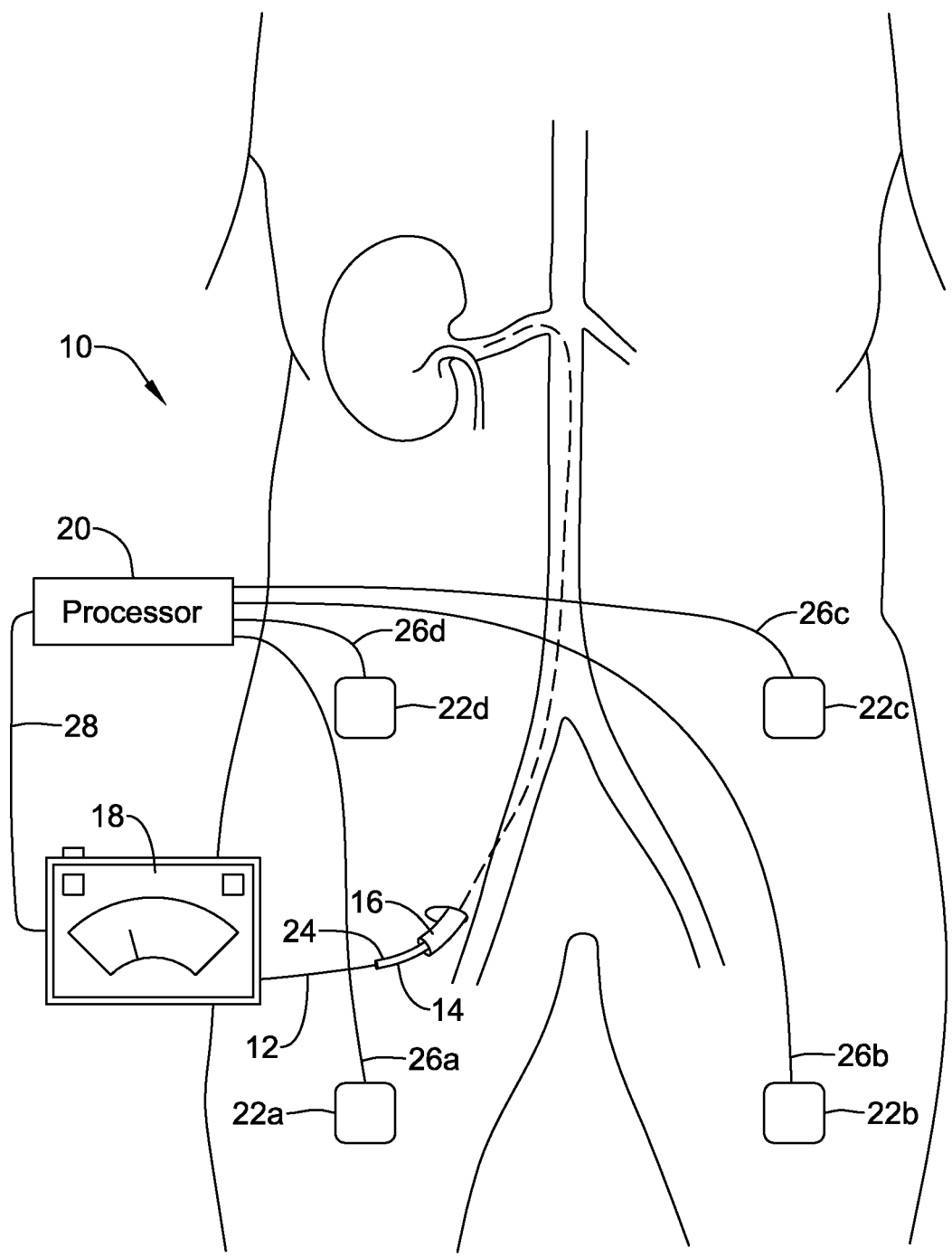
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Certain treatments require the temporary or permanent interruption or modification of select nerve function. One example treatment is renal nerve ablation, which is sometimes used to treat conditions related to congestive heart failure or hypertension. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

While the devices and methods described herein are discussed relative to renal nerve modulation, it is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, tumor ablation, benign prostatic hyperplasia therapy, nerve excitation or blocking or ablation, modulation of muscle activity, hyperthermia or other warming of tissues, etc. In some instances, it may be desirable to ablate perivascular renal nerves using a radiofrequency electrode.

While the devices and methods described herein are discussed relative to renal nerve modulation through a blood vessel wall, it is contemplated that the devices and methods may be used in other applications where nerve modulation and/or ablation are desired. The term modulation refers to ablation and other techniques that may alter the function of affected nerves.

In all circuits, completion of the circuit is made using the path of least resistance. In radiofrequency ablation circuits involving the body, the path of least resistance is often through muscle. Because muscle is of lower impedance than connective tissue, the propensity for generating inconsistent lesions may be greater if connective, fatty, and muscular tissues are all present. In a case such as this, the lesions generated may be of lesser or greater depth based upon tissue presence and type. Also, bowel or psoas muscle burns may occur.

FIG. 1 is a schematic view of an illustrative renal nerve modulation system 10 in situ. System 10 may include an element 12 for providing power to a nerve modulation element disposed about and/or within a central elongate shaft 14 and, optionally, within a sheath 16. A proximal end of element 12 may be connected to a control and power element 18, which supplies the necessary electrical energy to activate the one or more modulation elements or electrodes at or near a distal end of the element 12. When suitably activated, the electrode(s) are capable of ablating tissue. The terms electrode and electrode(s) may be considered to be equivalent to elements capable of ablating adjacent tissue. In some instances, one or more return electrode patches 22a, 22b, 22c, 22d (collectively 22a-d) may be supplied on the legs or at another conventional location on the patient's body to complete the circuit. The control and power element 18 may include monitoring elements to monitor parameters such as power, temperature, voltage, pulse size, and/or shape and other suitable parameters as well as suitable controls for performing the desired procedure. In some instances, the power element 18 may control a radio frequency (RF) ablation electrode and/or one or more sensing electrode(s). It is contemplated that more than one power element 18 may be provided. The ablation electrode may be configured to operate at a frequency of approximately 460 kHz. It is contemplated that any desired frequency in the RF range may be used, for example, from 100-500 kHz. However, it is contemplated that different types of energy outside the RF spectrum may be used as desired, for example, but not limited to ultrasound, microwave, and laser to perform the ablation. While the term ablation electrode is used herein, it is contemplated that the modulation element and modulation frequency may be selected according to the energy used to perform the ablation. For example, when ultrasound energy is used, an ultrasonic transducer may be selected as the modulation element and modulation frequencies may be in the MHz range.

The elongate shaft 14 may extend distally from a proximal end 24 to a distal end configured to be advanced within a body lumen to a desired treatment region. The proximal end 24 of the elongate shaft 14 may include a hub (not explicitly shown) attached thereto for connecting other treatment devices or providing a port for facilitating other treatments. It is contemplated that the stiffness of the elongated shaft 14 may be modified to form modulation system 10 for use in various vessel diameters and various locations within the vascular tree. To this end, the material used for manufacturing the elongated shaft 14 may include any suitable biocompatible material such as, but are not limited to, polymers, metals, alloys, either in combination or alone. The material employed may have enough stiffness for use in various lumen diameters, and sufficient flexibility to maneuver through tortuous and/or stenotic lumens, avoiding any undesirable tissue injuries.

The elongate shaft 14 may further include one or more lumens extending therethrough. For example, the elongate shaft 14 may include a guidewire lumen and/or one or more auxiliary lumens. The lumens may be configured in any way known in the art. For example, the guidewire lumen may extend the entire length of the elongate shaft 14 such as in an over-the-wire catheter or may extend only along a distal portion of the elongate shaft 14 such as in a single operator exchange (SOE) catheter. These examples are not intended to be limiting, but rather examples of some possible configurations. While not explicitly shown, the modulation system 10 may further include temperature sensors/wire, an infusion lumen, radiopaque marker bands, fixed guidewire tip, a guidewire lumen, external sheath and/or other components to facilitate the use and advancement of the system 10 within the vasculature.

While not explicitly shown, the modulation system 10 may be include one or more ablation electrode(s) disposed on the outer surface of the elongate shaft 14 adjacent to the distal end region. However, the ablation electrode(s) may be placed at any longitudinal location along the elongate shaft 14 desired. It is further contemplated that in some embodiments, the modulation system 10 may include one or more positioning elements, such as an inflatable balloon or expandable basket, positioned adjacent the distal end the elongate shaft 14 to assist in orienting the one or more electrode(s). In some instances, the ablation electrode(s) may be positioned on a surface of the one or more positioning elements. It is contemplated that ablation electrode(s) may be positioned on an exterior surface of an inflatable balloon or on the framework of an expandable basket. In other instances, the ablation electrode(s) may be positioned within an inflatable balloon, such as on an elongate shaft extending therethough or on an interior surface.

It is contemplated that the modulation system 10 may include any number of ablation electrode(s) desired, such as, but not limited to, one, two, three, four, or more. If multiple ablation electrode(s) are provided, the ablation electrode(s) may be longitudinally, radially and/or circumferentially spaced as desired. In some instances, the ablation electrode may be a circumferential electrode extending around the outer perimeter of the elongate shaft 14. A circumferential electrode may allow for circumferential ablation while reducing and/or eliminating the need for circumferential repositioning of the electrode and/or elongate shaft 14. In some embodiments, the ablation electrode may not extend all the way around the perimeter of the elongate shaft 14. It is contemplated that multiple ablation electrode(s) may be circumferentially positioned around the perimeter of the elongate shaft 14 to reduce and/or eliminate the need to circumferentially reposition the elongate shaft 14 to perform 360° ablation.

The ablation electrode(s) may be connected to the control unit 18 by an insulated electrical conductor, such as element 12 shown in FIG. 1. Once the modulation system 10 has been advanced to the treatment region, energy may be supplied to the ablation electrode(s). The amount of energy delivered to the ablation electrode may be determined by the desired treatment as well as the feedback obtained from the system 10. The power level and duration of the ablation may be adjusted accordingly based on the impedance of the tissue. For example, more energy may result in a larger, deeper lesion. As voltage is applied to the ablation electrode current may pass through tissue proximate the treatment region and additional body tissue between the treatment region and the skin to the skin-contact ground pads 22a-d. While the ground pads 22a-d are illustrated as being positioned on a single side (either posterior or anterior) of the body, it is contemplated that the ground pads may be positioned on either or both sides of the body, as desired. While the system 10 is illustrated as including four ground pads 22a-d, it is contemplated that there may be fewer than four or more than four ground pads as desired. In some instances, it is contemplated that the system 10 may include eight or more ground pads. For example, in some embodiments, the system 10 may include four ground pads positioned on the posterior side of the body and four ground pads positioned on the anterior side of the body. The ground pads may be evenly distributed about the desired treatment region. In some instances, two ground pads may be placed on the upper torso on the anterior side and two ground pads may be placed on the lower torso on the anterior side. Similarly, two ground pads may be placed on the upper torso on the posterior side and two ground pads may be placed on the lower torso on the posterior side. However, this arrangement is merely exemplary. It is contemplated that any number of ground pads may be arranged in any suitable manner for the desired treatment.

The body tissue may comprise adventitia and connective tissues, nerves, fat, fluid, etc. in addition to the muscular vessel wall. Each pad 22a, 22b, 22c, 22d may have a given impedance to complete the electrical circuit and each pad's impedance may differ based upon the tissue types which exist between the treatment region and the grounding (pad) location. Each ground pad 22a, 22b, 22c, 22d may be connected to individual channels of a processor or processing unit 20 through separate electrical conductors 26a, 26b, 26c, 26d. In some instances, the processor 20 may be electrically connected to or otherwise in communication with the power unit 18 via a grounding channel out 28. As each pad 22a, 22b, 22c, 22d may be individually connected to a separate grounding in channels of the processor 20, the resistance of the electrical connections 26a, 26b, 26c, 26d may be individually adjusted. For example, it is contemplated that each channel may include a separate variable resistor for individually adjusting each individual circuit. It is contemplated that the processor 20 may include any number of channels desired such that the electrical connections between the processor 20 and the ground pads 22a-d may be individually adjusted.

As noted above each ground pad 22a, 22b, 22c, 22d may have a certain impedance to complete the circuit (e.g. the path between the ablation electrode disposed within the body and the ground pad located on an exterior surface of the body). As current follows the path of least resistance, it is contemplated that current will preferentially travel between the ablation electrode and the ground pad that has the least amount of impedance to complete the circuit. As such, inconsistent or unintended lesions may occur. This may result in variability in lesion size and depth between treatment locations and from patient to patient. It is contemplated that once connected, the processor 20 may increase the impedance of all circuits to an identical level such that current is evenly distributed between the ablation electrode and the ground pads 22a-d. An illustrative, but non-limiting, example is given in Table 1 below. The impedance given for each ground pad is merely exemplary and is not intended to be limiting in any manner or indicative of actual impedance between the treatment region and the illustrated position of the pad.

TABLE 1

|  | Impedance (Initial) | Impedance (Post Processing) |
| --- | --- | --- |
| Pad 1 (22a) | 97 Ω | 145 Ω |
| Pad 2 (22b) | 145 Ω | 145 Ω |
| Pad 3 (22c) | 123 Ω | 145 Ω |
| Pad 4 (22d) | 111 Ω | 145 Ω |

The values in the "Impedance (Initial)" column are the impedance values as they may naturally occur while the values in the "Impedance (Post Processing)" column are the impedance values after the processor 20 has adjusted the impedance of the individual circuits. As can be seen, prior to processing, the impedance between each ground pad 22a, 22b, 22c, 22d and the ablation electrode is different for each ground pad 22a, 22b, 22c, 22d. Without any adjustments, it is contemplated that the lowest impedance pathway (e.g. in this example, between bond pad 22a and the ablation electrode) may draw current in the direction of pad 22a. However, the processor 20 may be used to increase the circuit impedance for pads 22a, 22c, 22d to be equivalent to pad 22b. It is contemplated that the processor 20 may electronically add impedance to the circuit by varying the resistance between the ground pad and the processor 20 such that current is evenly distributed between the ablation electrode and the ground pads 22a-d. For example, the energy may travel spherically from the ablation electrode. In some instances, the processor 20 may use a number of variable resistors to add impedance to the circuits. It is further contemplated that the circuit impedance may be further manipulated by repositioning the ground pads 22a, 22b, 22c or 22d. In some instances, the ground pads 22a-d may be strategically located on a patient's body to control the direction of current flow. As the current path can be manipulated based on the impedance of the circuit, the location of the ground pads 22a-d or a combination of the impedance and the location of the ground pads 22a-d, the size and shape of a lesion may be more readily controlled thus reducing and/or eliminating unintended lesions.

In some embodiments, the processor 20 may automatically balance and/or adjust the impedance of the circuits prior to applying power and/or during the ablation procedure. It is contemplated that in some instances, the impedance will not be allowed to automatically adjust once the power has been applied to the ablation electrode. However, the impedance between the ablation electrode and the ground pads 22a-d may be monitored during the ablation procedure. It is contemplated that the modulation system 10 may include set point limits for the ablation procedure variables, such as but not limited to power and temperature. For example, in some instances, the power supplied by the power unit 18 may not exceed a predetermined threshold and/or the power unit may include a control algorithm to maintain the temperature of the target region from exceeding a predetermined threshold temperature.

It is further contemplated that a modulation system 10 that utilizes multiple ablation electrodes powered by a single power source may experience variability in the impedance of each ablation or active electrode. Such variability in the impedance of the ablation electrodes may result in variability of the lesion size and/or depth from each electrode. Providing multiple ground locations, such as ground pads 22a-d, each with modulated impedance, may draw current/power more evenly through each ablation electrode. For example, the energy may travel spherically from the ablation electrode. Manipulation of the current paths may reduce variability in the lesion size and depth resulting in more consistent lesions at the treatment site.

In some embodiments, when multiple active or ablation electrodes are provided at or near the distal end of element 12, the system the system 10 may be operated in a bipolar mode. In this instance, two (or more) electrodes disposed at the treatment location may be 180° out of phase such that one electrode acts as the ground electrode (e.g. one cathode and one anode). It is contemplated that the processor 20 may automatically balance and/or adjust the impedance of the circuits prior to applying power in a similar manner as described above. For example, the processor 20 may electronically add impedance to circuits, as necessary, by varying the resistance between the active electrode functioning as the ground electrode and the processor 20 such that current is evenly distributed between the ablation electrodes and ground electrodes.

The modulation system 10 may be advanced through the vasculature in any manner known in the art. For example, system 10 may include a guidewire lumen to allow the system 10 to be advanced over a previously located guidewire. In some embodiments, the modulation system 10 may be advanced, or partially advanced, within a guide sheath such as the sheath 16. Once the ablation electrode(s) of the modulation system 10 have been placed adjacent to the desired treatment area, positioning mechanisms may be deployed, such as centering baskets, if so provided.

Once the modulation system 10 has been advanced to the treatment region, energy may be supplied to the ablation electrode(s). The amount of energy delivered to the ablation electrode(s) may be determined by the desired treatment as well as the feedback provided by the system 10. As the energy is supplied to the electrode(s), the processing unit 20 may analyze the impedance of the circuits formed by each ground pad 22a, 22b, 22c, 22d. The processing unit 20 may then add impedance to one or more circuits such that all circuits have the same impedance. It is contemplated that as ablation of desired treatment region progresses, the impedance of the circuits may change due to the formation of a lesion. Thus, the processor 20 may be configure to continuously adjust the resistance of each of the circuits formed between the ablation electrode(s) and the ground pads 22a, 22b, 22c, 22d throughout the duration of the ablation procedure. In some instances, the processor 20 may be configured to adjust the resistance of the each of the circuits at predefined time intervals.

In some instances, the elongated shaft 14 may be rotated and additional ablation can be performed at multiple locations around the circumference of the vessel. In some instances, a slow automated "rotisserie" rotation can be used to work around the circumference of the vessel, or a faster spinning can be used to simultaneously ablate around the entire circumference. The spinning can be accomplished with a micro-motor or by spinning a drive shaft. The number of times the elongated shaft 14 is rotated at a given longitudinal location may be determined by the number and size of the ablation electrode(s) present. Once a particular location has been ablated, it may be desirable to perform further ablation procedures at different longitudinal locations. Once the elongated shaft 14 has been longitudinally repositioned, energy may once again be delivered to the ablation electrode(s). If necessary, the elongated shaft 14 may be rotated to perform ablation around the circumference of the vessel at each longitudinal location. This process may be repeated at any number of longitudinal locations desired. It is contemplated that in some embodiments, the system 10 may include ablation electrode(s) at various positions along the length of the modulation system 10 such that a larger region may be treated without longitudinal displacement of the elongated shaft 14.

Figure 2:
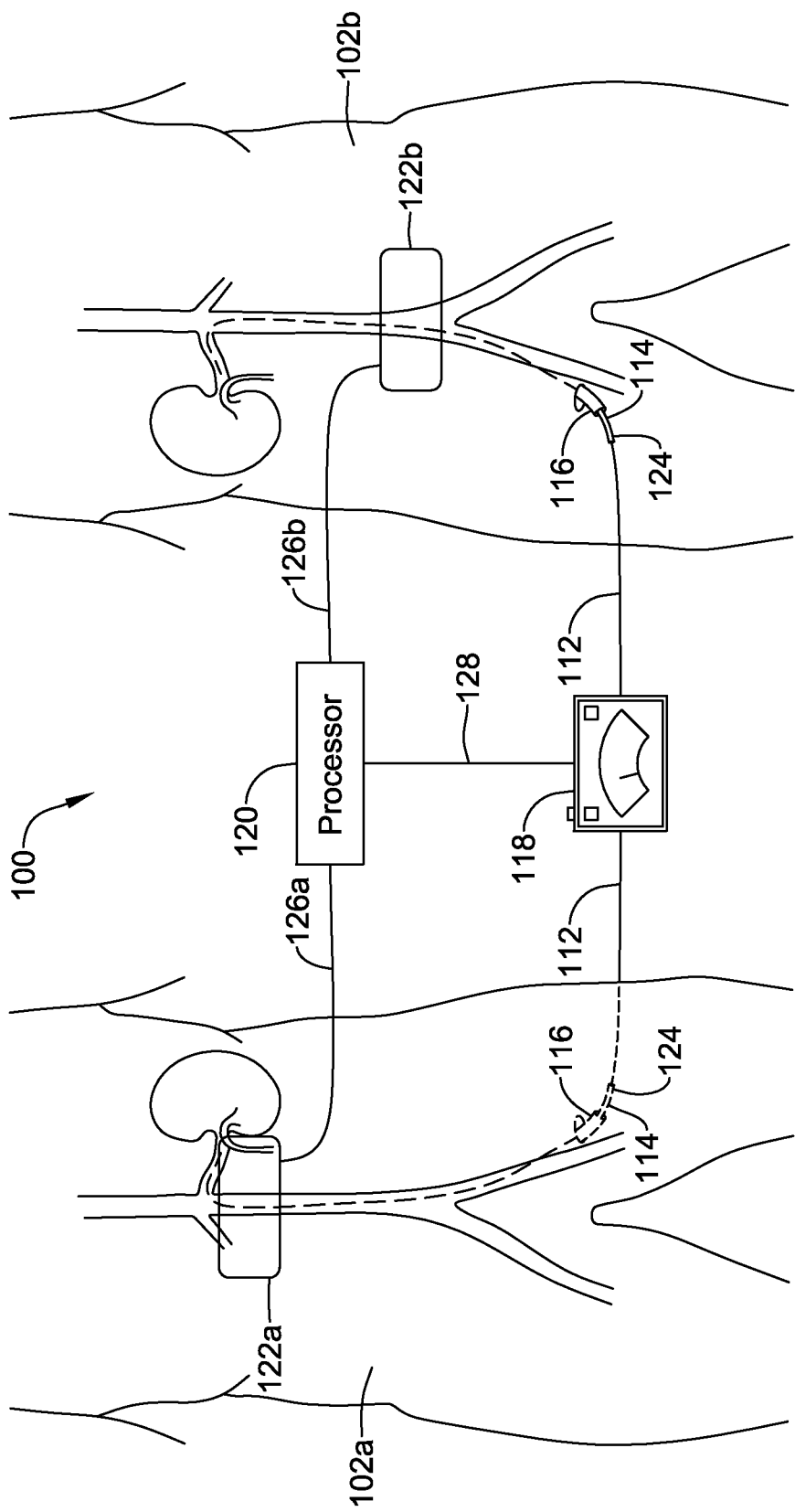
FIG. 2 is another schematic view illustrating a renal nerve modulation system in situ.

FIG. 2 is a schematic view of another illustrative renal nerve modulation system 100 in situ. System 100 may be similar in form and function to other modulation systems discussed herein. System 100 may include an element 112 for providing power to a nerve modulation element disposed about and/or within a central elongate shaft 114 and, optionally, within a sheath 116. A proximal end of element 112 may be connected to a control and power element 18, which supplies the necessary electrical energy to activate the one or more modulation elements or electrode(s) at or near a distal end of the element 112. When suitably activated, the electrode(s) are capable of ablating tissue. In some instances, one or more return electrode patches 122a, 122b, (collectively 122a-b) may be supplied on the patient's body to complete the circuit. In some instances, a first return electrode 122a may be supplied on the posterior side 102a of the patient's body while a second return electrode 122b may be supplied on the anterior side 102b of the patient's body.

The control and power element 118 may include monitoring elements to monitor parameters such as power, temperature, voltage, pulse size, and/or shape and other suitable parameters as well as suitable controls for performing the desired procedure. In some instances, the power element 118 may control a radio frequency (RF) ablation electrode and/or one or more sensing electrode(s). It is contemplated that more than one power element 118 may be provided. The ablation electrode may be configured to operate at a frequency of approximately 460 kHz. It is contemplated that any desired frequency in the RF range may be used, for example, from 100-500 kHz. However, it is contemplated that different types of energy outside the RF spectrum may be used as desired, for example, but not limited to ultrasound, microwave, and laser to perform the ablation. While the term ablation electrode is used herein, it is contemplated that the modulation element and modulation frequency may be selected according to the energy used to perform the ablation. For example, when ultrasound energy is used, an ultrasonic transducer may be selected as the modulation element and modulation frequencies may be in the MHz range.

The elongate shaft 114 may extend distally from a proximal end 124 to a distal end configured to be advanced within a body lumen to a desired treatment region. The proximal end 124 of the elongate shaft 114 may include a hub (not explicitly shown) attached thereto for connecting other treatment devices or providing a port for facilitating other treatments. It is contemplated that the stiffness of the elongate shaft 114 may be modified to form a modulation system 100 for use in various vessel diameters and various locations within the vascular tree. The elongate shaft 114 may further include one or more lumens extending therethrough. For example, the elongate shaft 114 may include a guidewire lumen and/or one or more auxiliary lumens. The lumens may be configured in any way known in the art. While not explicitly shown, the modulation system 100 may further include temperature sensors/wire, an infusion lumen, radiopaque marker bands, fixed guidewire tip, a guidewire lumen, external sheath and/or other components to facilitate the use and advancement of the system 100 within the vasculature.

While not explicitly shown, the modulation system 100 may be include one or more ablation electrode(s) disposed on the outer surface of the elongate shaft 114 adjacent to the distal end region. However, the ablation electrode(s) may be placed at any longitudinal location along the elongate shaft 114 desired. It is further contemplated that in some embodiments, the modulation system 100 may include one or more positioning elements, such as an inflatable balloon or expandable basket, positioned adjacent the distal end the elongate shaft 114 to assist in orienting the one or more electrode(s). In some instances, the ablation electrode(s) may be positioned on a surface of the one or more positioning elements. It is contemplated that ablation electrode(s) may be positioned on an exterior surface of an inflatable balloon or on the framework of an expandable basket. In other instances, the ablation electrode(s) may be positioned within an inflatable balloon, such as on an elongate shaft extending therethough or on an interior surface.

It is contemplated that the modulation system 100 may include any number of ablation electrode(s) desired, such as, but not limited to, one, two, three, four, or more. If multiple ablation electrode(s) are provided, the ablation electrode(s) may be longitudinally, radially and/or circumferentially spaced as desired. In some instances, the ablation electrode may be a circumferential electrode extending around the outer perimeter of the elongate shaft 114. A circumferential electrode may allow for circumferential ablation while reducing and/or eliminating the need for circumferential repositioning of the electrode and/or elongate shaft 114. In some embodiments, the ablation electrode may not extend all the way around the perimeter of the elongate shaft 114. It is contemplated that multiple ablation electrode(s) may be circumferentially positioned around the perimeter of the elongate shaft 114 to reduce and/or eliminate the need to circumferentially reposition the elongate shaft 114 to perform 360° ablation.

The ablation electrode(s) may be connected to the control unit 118 by an insulated electrical conductor, such as element 112 shown in FIG. 2. Once the modulation system 100 has been advanced to the treatment region, energy may be supplied to the ablation electrode(s). The amount of energy delivered to the ablation electrode may be determined by the desired treatment as well as the feedback obtained from the system 100. The power level and duration of the ablation may be adjusted accordingly based on the impedance of the tissue. For example, more energy may result in a larger, deeper lesion. As voltage is applied to the ablation electrode, current may pass through tissue proximate the treatment region and additional body tissue between the treatment region and the skin to the skin-contact ground pads 122*a*-*b*.

While the ground pads 122*a*-*b* are illustrated as being positioned on opposite sides (e.g. posterior and anterior) of the body, it is contemplated that the ground pads may be positioned on either or both sides of the body, as desired. While the system 100 is illustrated as including two ground pads 122*a*-*b*, it is contemplated that there may be fewer than two or more than two ground pads as desired. In some embodiments, the system 100 may include one, two, three, four or more ground pads positioned on each side 102*a*, 102*b* of the body. In some instances, while not explicitly shown, the ground pads 122*a*-*b* may be evenly distributed about the desired treatment region. However, it is contemplated that any number of ground pads may be arranged in any suitable manner for the desired treatment.

The body tissue may comprise adventitia and connective tissues, nerves, fat, fluid, etc. in addition to the muscular vessel wall. Each pad 122*a*, 122*b* may have a given impedance to complete the electrical circuit and each pad's impedance may differ based upon the tissue types which exist between the treatment region and the grounding (pad) location. Each ground pad 122*a*, 122*b* may be connected to individual channels of a processor or processing unit 120 through separate electrical conductors 126*a*, 126*b* to create individual circuits. In some instances, the processor 120 may be electrically connected to or otherwise in communication with the power unit 118 via a grounding channel out 128. As each pad 122*a*, 122*b* may be individually connected to separate grounding in channels of the processor 120, the resistance of the electrical connections 126*a*, 126*b* may be individually adjusted. For example, it is contemplated that each channel may include a separate variable resistor for individually adjusting each individual circuit. It is contemplated that the processor 120 may include any number of channels desired such that the electrical connections between the processor 120 and the ground pads 122*a*-*b* may be individually adjusted.

As noted above each ground pad 122*a*, 122*b* may have a certain impedance to complete the circuit (e.g. the path between the ablation electrode disposed within the body and the ground pad located on an exterior surface of the body). As current follows the path of least resistance, it is contemplated that current will preferentially travel between the ablation electrode and the ground pad that has the least amount of impedance to complete the circuit. As such, inconsistent or unintended lesions may occur. This may result in variability in lesion size and depth between treatment locations and from patient to patient. It is contemplated that once connected, the processor 120 may increase the impedance of all circuits to an identical level such that current is evenly distributed between the ablation electrode and the ground pads 122a-b. For example, the energy may travel spherically from the ablation electrode. The processor 120 may electronically add impedance to the circuit(s) by varying the resistance between the ground pads 122a-b and the processor 120. In some instances, the processor 120 may use a number of variable resistors to add impedance to the circuits. It is further contemplated that the circuit impedance may be further manipulated by repositioning the ground pads 122a, 122b. In some instances, the ground pads 122a-b may be strategically located on a patient's body to control the direction of current flow. As the current path can be manipulated based on the impedance of the circuit, the location of the ground pads 122a-b or a combination of the impedance and the location of the ground pads 122a-b, it is contemplated that the size and shape of a lesion may be more readily controlled thus reducing and/or eliminating unintended lesions.

It is further contemplated that a modulation system 100 that utilizes multiple ablation electrodes powered by a single power source may experience variability in the impedance of each ablation or active electrode. Such variability in the impedance of the ablation electrodes may result in variability of the lesion size and/or depth from each electrode. Providing multiple ground locations, such as ground pads 122a-b, each with modulated impedance, may draw current/power more evenly through each ablation electrode. For example, the energy may travel spherically from the ablation electrode. Manipulation of the current paths may reduce variability in the lesion size and depth resulting in more consistent lesions at the treatment site.

The modulation system 100 may be advanced through the vasculature in any manner known in the art. For example, system 100 may include a guidewire lumen to allow the system 100 to be advanced over a previously located guidewire. In some embodiments, the modulation system 100 may be advanced, or partially advanced, within a guide sheath such as the sheath 116. Once the ablation electrode(s) of the modulation system 100 have been placed adjacent to the desired treatment area, positioning mechanisms may be deployed, such as centering baskets, if so provided.

Once the modulation system 100 has been advanced to the treatment region, energy may be supplied to the ablation electrode(s). The amount of energy delivered to the ablation electrode(s) may be determined by the desired treatment as well as the feedback provided by the system 100. As the energy is supplied to the electrode(s), the processing unit 120 may analyze the impedance of the circuits formed by each ground pad 122a, 122b. The processing unit 120 may then add impedance to one or more circuits such that all circuits have the same impedance. It is contemplated that as ablation of desired treatment region progresses, the impedance of the circuits may change due to the formation of a lesion. Thus, the processor 120 may be configure to continuously adjust the resistance of each of the circuits formed between the ablation electrode(s) and the ground pads 122a, 122b throughout the duration of the ablation procedure. In some instances, the processor 120 may be configured to adjust the resistance of the each of the circuits at predefined time intervals.

In some instances, the elongated shaft 114 may be rotated and additional ablation can be performed at multiple locations around the circumference of the vessel. In some instances, a slow automated "rotisserie" rotation can be used to work around the circumference of the vessel, or a faster spinning can be used to simultaneously ablate around the entire circumference. The spinning can be accomplished with a micro-motor or by spinning a drive shaft. The number of times the elongated shaft 114 is rotated at a given longitudinal location may be determined by the number and size of the ablation electrode(s) present. Once a particular location has been ablated, it may be desirable to perform further ablation procedures at different longitudinal locations. Once the elongated shaft 114 has been longitudinally repositioned, energy may once again be delivered to the ablation electrode(s). If necessary, the elongated shaft 114 may be rotated to perform ablation around the circumference of the vessel at each longitudinal location. This process may be repeated at any number of longitudinal locations desired. It is contemplated that in some embodiments, the system 100 may include ablation electrode(s) at various positions along the length of the modulation system 100 such that a larger region may be treated without longitudinal displacement of the elongated shaft 114.

FIG. 3 is a schematic view of another illustrative renal nerve modulation system 200 in situ. System 200 may be similar in form and function to other modulation systems discussed herein. System 200 may include an element 212 for providing power to a nerve modulation element disposed about and/or within a central elongate shaft 214 and, optionally, within a sheath 216. A proximal end of element 212 may be connected to a control and power element 18, which supplies the necessary electrical energy to activate the one or more modulation elements or electrode(s) at or near a distal end of the element 212. When suitably activated, the electrode(s) are capable of ablating tissue. In some instances, one or more return electrode patches 222a, 222b, 222c, 222d, 222e, 222c, 222d, 222e (collectively 222a-e) may be supplied on the patient's body to complete the circuit. In some instances, first and second return electrodes 222a, 222b, 222c, 222d, 222e may be supplied on the posterior side 202a of the patient's body while third and fourth return electrodes 222d, 222e may be supplied on the anterior side 202b of the patient's body. In some instances, a fifth electrode 222c may be supplied on a lateral side of the patient's body such that it is positioned between the posterior 202a and anterior 202b sides. While not explicitly shown, it is contemplated that one or more additional electrodes may also be supplied on the opposite lateral side of the patient's body.

The control and power element 218 may include monitoring elements to monitor parameters such as power, temperature, voltage, pulse size, and/or shape and other suitable parameters as well as suitable controls for performing the desired procedure. In some instances, the power element 218 may control a radio frequency (RF) ablation electrode and/or one or more sensing electrode(s). It is contemplated that more than one power element 218 may be provided. The ablation electrode may be configured to operate at a frequency of approximately 460 kHz. It is contemplated that any desired frequency in the RF range may be used, for example, from 100-500 kHz. However, it is contemplated that different types of energy outside the RF spectrum may be used as desired, for example, but not limited to ultrasound, microwave, and laser to perform the ablation. While the term ablation electrode is used herein, it is contemplated that the modulation element and modulation frequency may be selected according to the energy used to perform the ablation. For example, when ultrasound energy is used, an ultrasonic transducer may be selected as the modulation element and modulation frequencies may be in the MHz range.

The elongate shaft 214 may extend distally from a proximal end 224 to a distal end configured to be advanced within a body lumen to a desired treatment region. The proximal end 224 of the elongate shaft 214 may include a hub (not explicitly shown) attached thereto for connecting other treatment devices or providing a port for facilitating other treatments. It is contemplated that the stiffness of the elongate shaft 214 may be modified to form a modulation system 200 for use in various vessel diameters and various locations within the vascular tree. The elongate shaft 214 may further include one or more lumens extending therethrough. For example, the elongate shaft 214 may include a guidewire lumen and/or one or more auxiliary lumens. The lumens may be configured in any way known in the art. While not explicitly shown, the modulation system 200 may further include temperature sensors/wire, an infusion lumen, radiopaque marker bands, fixed guidewire tip, a guidewire lumen, external sheath and/or other components to facilitate the use and advancement of the system 200 within the vasculature.

While not explicitly shown, the modulation system 200 may be include one or more ablation electrode(s) disposed on the outer surface of the elongate shaft 214 adjacent to the distal end region. However, the ablation electrode(s) may be placed at any longitudinal location along the elongate shaft 214 desired. It is further contemplated that in some embodiments, the modulation system 200 may include one or more positioning elements, such as an inflatable balloon or expandable basket, positioned adjacent the distal end the elongate shaft 214 to assist in orienting the one or more electrode(s). In some instances, the ablation electrode(s) may be positioned on a surface of the one or more positioning elements. It is contemplated that ablation electrode(s) may be positioned on an exterior surface of an inflatable balloon or on the framework of an expandable basket. In other instances, the ablation electrode(s) may be positioned within an inflatable balloon, such as on an elongate shaft extending therethough or on an interior surface.

It is contemplated that the modulation system 200 may include any number of ablation electrode(s) desired, such as, but not limited to, one, two, three, four, or more. If multiple ablation electrode(s) are provided, the ablation electrode(s) may be longitudinally, radially and/or circumferentially spaced as desired. In some instances, the ablation electrode may be a circumferential electrode extending around the outer perimeter of the elongate shaft 214. A circumferential electrode may allow for circumferential ablation while reducing and/or eliminating the need for circumferential repositioning of the electrode and/or elongate shaft 214. In some embodiments, the ablation electrode may not extend all the way around the perimeter of the elongate shaft 214. It is contemplated that multiple ablation electrode(s) may be circumferentially positioned around the perimeter of the elongate shaft 214 to reduce and/or eliminate the need to circumferentially reposition the elongate shaft 214 to perform 360° ablation.

The ablation electrode(s) may be connected to the control unit 218 by an insulated electrical conductor, such as element 212 shown in FIG. 2. Once the modulation system 200 has been advanced to the treatment region, energy may be supplied to the ablation electrode(s). The amount of energy delivered to the ablation electrode may be determined by the desired treatment as well as the feedback obtained from the system 200. The power level and duration of the ablation may be adjusted accordingly based on the impedance of the tissue. For example, more energy may result in a larger, deeper lesion. As voltage is applied to the ablation electrode, current may pass through tissue proximate the treatment region and additional body tissue between the treatment region and the skin to the skin-contact ground pads 222a-e.

While the ground pads 222a-e are illustrated as being positioned on multiple sides (e.g. posterior, anterior, and lateral) of the body, it is contemplated that the ground pads 222a-e may be positioned on each side (posterior, anterior, or lateral) individually or the ground pads 222a-e may be positioned on any combination of the posterior, anterior, and lateral sides, as desired. While the system 200 is illustrated as including five ground pads 222a-e, it is contemplated that there may be fewer than five or more than five ground pads as desired. In some embodiments, the system 200 may include one, two, three, four or more ground pads positioned on each side (posterior, anterior, or lateral) of the body. While not explicitly shown, it is contemplated that one or more additional electrodes may also be supplied on the opposite lateral side of the patient's body. It is contemplated that placing additional ground pads on a lateral side of the body may allow for more even current distribution by drawing current in additional directions. In some instances, while not explicitly shown, the ground pads 222a-e may be evenly distributed about the desired treatment region(s). However, it is contemplated that any number of ground pads may be arranged in any suitable manner for the desired treatment.

In some instances, the distribution of the ground pads 222a-e may be selected to allow for a zone control option. For example, if nerve ablation is desired on both the right and left renal arteries, it may be desirable to have ground pads positioned on both lateral sides of the body in addition to the anterior and posterior sides. During ablation of the right renal nerves, ground pads on the right lateral side of the body may be activated in addition to any ground pads on the anterior and/or posterior sides while ground pads on the left lateral side of the body remain inactive. Similarly, the during ablation of the left renal nerves, ground pads on the left lateral side of the body may be activated in addition to any ground pads on the anterior and/or posterior sides while ground pads on the right lateral side of the body remain inactive. The processor 220 may include a feedback loop to allow for selection between multiple treatment zones. However, it is contemplated that the ground pads may be assigned zones based on the desired treatment, and the system 200 is not intended to be limited to the example zones provided.

The body tissue may comprise adventitia and connective tissues, nerves, fat, fluid, etc. in addition to the muscular vessel wall. Each pad 222a, 222b, 222c, 222d, 222e may have a given impedance to complete the electrical circuit and each pad's impedance may differ based upon the tissue types which exist between the treatment region and the grounding (pad) location. Each ground pad 222a, 222b, 222c, 222d, 222e may be connected to individual channels of a processor or processing unit 220 through separate electrical conductors 226a, 226b, 226c, 226d, 226e to create individual circuits. In some instances, the processor 220 may be electrically connected to or otherwise in communication with the power unit 218 via a grounding channel out 228. As each pad 222a, 222b, 222c, 222d, 222e may be individually connected to separate grounding in channels of the processor 220, the resistance of the electrical connections 226a, 226b, 226c, 226d, 226e may be individually adjusted. For example, it is contemplated that each channel may include a separate variable resistor for individually adjusting each individual circuit. It is contemplated that the processor 220 may include any number of channels desired such that the electrical connections between the processor 220 and the ground pads 222a-e may be individually adjusted. Further, the processor 220 may be configured to disconnect one or more ground pads 222a-e from the circuit such that the ground pads 222a-e may be activated as desired, such as to create zone control.

As noted above each ground pad 222a, 222b, 222c, 222d, 222e may have a certain impedance to complete the circuit (e.g. the path between the ablation electrode disposed within the body and the ground pad located on an exterior surface of the body). As current follows the path of least resistance, it is contemplated that current will preferentially travel between the ablation electrode and the ground pad that has the least amount of impedance to complete the circuit. As such, inconsistent or unintended lesions may occur. This may result in variability in lesion size and depth between treatment locations and from patient to patient. It is contemplated that once connected, the processor 220 may increase the impedance of all circuits to an identical level such that current is evenly distributed between the ablation electrode and the ground pads 222a-e. For example, the energy may travel spherically from the ablation electrode. The processor 220 may electronically add impedance to the circuit(s) by varying the resistance between the ground pads 222a-e and the processor 220. In some instances, the processor 220 may use a number of variable resistors to add impedance to the circuits. It is further contemplated that the circuit impedance may be further manipulated by repositioning the ground pads 222a, 222b, 222c, 222d, 222e. In some instances, the ground pads 222a-e may be strategically located on a patient's body to control the direction of current flow. As the current path can be manipulated based on the impedance of the circuit, the location of the ground pads 222a-e or a combination of the impedance and the location of the ground pads 222a-e, it is contemplated that the size and shape of a lesion may be more readily controlled thus reducing and/or eliminating unintended lesions.

It is further contemplated that a modulation system 200 that utilizes multiple ablation electrodes powered by a single power source may experience variability in the impedance of each ablation or active electrode. Such variability in the impedance of the ablation electrodes may result in variability of the lesion size and/or depth from each electrode. Providing multiple ground locations, such as ground pads 222a-e, each with modulated impedance, may draw current/power more evenly through each ablation electrode. For example, the energy may travel spherically from the ablation electrode. Manipulation of the current paths may reduce variability in the lesion size and depth resulting in more consistent lesions at the treatment site.

The modulation system 200 may be advanced through the vasculature in any manner known in the art. For example, system 200 may include a guidewire lumen to allow the system 200 to be advanced over a previously located guidewire. In some embodiments, the modulation system 200 may be advanced, or partially advanced, within a guide sheath such as the sheath 216. Once the ablation electrode(s) of the modulation system 200 have been placed adjacent to the desired treatment area, positioning mechanisms may be deployed, such as centering baskets, if so provided.

Once the modulation system 200 has been advanced to the treatment region, energy may be supplied to the ablation electrode(s). The amount of energy delivered to to the ablation electrode(s) may be determined by the desired treatment as well as the feedback provided by the system 200. As the energy is supplied to the electrode(s), the processing unit 220 may analyze the impedance of the circuits formed by each ground pad 222a, 222b, 222c, 222d, 222e. The processing unit 220 may then add impedance to one or more circuits such that all circuits have the same impedance. It is contemplated that as ablation of desired treatment region progresses, the impedance of the circuits may change due to the formation of a lesion. Thus, the processor 220 may be configure to continuously adjust the resistance of each of the circuits formed between the ablation electrode(s) and the ground pads 222a, 222b, 222c, 222d, 222e throughout the duration of the ablation procedure. In some instances, the processor 220 may be configured to adjust the resistance of the each of the circuits at predefined time intervals.

In some instances, the elongated shaft 214 may be rotated and additional ablation can be performed at multiple locations around the circumference of the vessel. In some instances, a slow automated "rotisserie" rotation can be used to work around the circumference of the vessel, or a faster spinning can be used to simultaneously ablate around the entire circumference. The spinning can be accomplished with a micro-motor or by spinning a drive shaft. The number of times the elongated shaft 214 is rotated at a given longitudinal location may be determined by the number and size of the ablation electrode(s) present. Once a particular location has been ablated, it may be desirable to perform further ablation procedures at different longitudinal locations. Once the elongated shaft 214 has been longitudinally repositioned, energy may once again be delivered to the ablation electrode(s). If necessary, the elongated shaft 214 may be rotated to perform ablation around the circumference of the vessel at each longitudinal location. This process may be repeated at any number of longitudinal locations desired. It is contemplated that in some embodiments, the system 200 may include ablation electrode(s) at various positions along the length of the modulation system 200 such that a larger region may be treated without longitudinal displacement of the elongated shaft 214.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method for performing intravascular nerve modulation at a target region in a lumen of a subject using a nerve modulation system comprising: an elongate shaft having a proximal end region and a distal end region; one or more ablation electrodes positioned adjacent the distal end region of the elongate shaft; two or more ground pads; a control unit electrically coupled to the one or more ablation electrodes; and a processor electrically coupled to the two or more ground pads; the method comprising:
positioning the two or more ground pads on a surface of a body of the subject at locations distributed about the target region, thereby controlling a direction of current flow between the one or more ablation electrodes and each of the two or more ground pads;
advancing the distal end region through the lumen such that the distal end region is adjacent to the target region;
applying a voltage to the one or more ablation electrodes, wherein current flows between the one or more ablation electrodes and each of the two or more ground pads to form individual circuits;
monitoring the impedance of each of the individual circuits; and adjusting the resistance of at least one of the individual circuits such that each of the individual circuits has approximately the same impedance.

2. The method of claim 1, wherein the impedance of each circuit is variable.

3. The method of claim 1, wherein adjusting the resistance of at least one of the circuits comprises adding resistance to the at least one circuit.

4. The method of claim 3, wherein the processor electronically adds resistance to the circuit.

5. The method of claim 1, wherein current flow is evenly distributed between the one or more ablation electrodes and the two or more ground pads.

6. The method of claim 1, wherein current flows spherically from the one or more ablation electrodes.

7. The method of claim 1, wherein the two or more ground pads are evenly distributed about the desired treatment region.

8. An intravascular nerve modulation system comprising:
an elongate shaft having a proximal end region and a distal end region;
an ablation electrode positioned adjacent the distal end region of the elongate shaft;
a plurality of ground pads;
a control unit electrically coupled to the ablation electrode and configured to apply a voltage to the ablation electrode such that energy flows between the ablation electrode and each of the plurality of ground pads, thereby forming a plurality of individual circuits; and
a processor electrically coupled to each of the plurality of ground pads;
wherein the processor is configured to monitor an impedance of each of the individual circuits; and
wherein the processor is configured to modulate a resistance of each of the individual circuits such that each circuit has approximately the same impedance.

9. The intravascular nerve modulation system of claim 8, further comprising an additional ablation electrode.

10. The intravascular nerve modulation system of claim 8, wherein the at least two ground pads includes a first ground pad and a second ground pad, and wherein the first ground pad is configured to be positioned on a subject's adjacent a first side of a desired treatment location and the second ground pad is configured to be positioned in the subject's body adjacent a second side of the desired treatment location.

11. A method for performing intravascular nerve modulation at a desired treatment location in a body of a subject using a nerve modulation system comprising: an elongate shaft having a proximal end region and a distal end region; an ablation electrode positioned adjacent the distal end region of the elongate shaft; a plurality of ground pads; a control unit electrically coupled to the ablation electrode and configured to apply a voltage to the ablation electrode such that current flows between the ablation electrode and each of the plurality of ground pads, thereby forming a plurality of individual circuits; and a processor electrically coupled to each of the plurality of ground pads; wherein the processor is configured to monitor an impedance of each of the individual circuits; and wherein the processor is configured to modulate a resistance of each of the individual circuits such that each circuit has approximately the same impedance; the method comprising:
advancing the distal end region through the lumen such that the distal end region is adjacent to the treatment location;
positioning a first ground pad of the plurality of ground pads on a surface of the subject's body adjacent a first side of the desired treatment location and positioning a second ground pad of the plurality of ground pads on the surface of the subject's body adjacent a second side of the desired treatment location thereby controlling a direction of current flow between the ablation electrode and the plurality of ground electrodes;
applying a voltage to the ablation electrode, wherein current flows between the ablation electrode and each of the plurality of ground pads to form a plurality of individual circuits;
monitoring the impedance of each of the individual circuits; and
modulating the resistance of at least one of the individual circuits such that each of the individual circuits has approximately the same impedance.

12. The method of claim 11, wherein the first ground pad is positioned on an anterior side of the subject's body and wherein the second ground pad is positioned on a posterior side of the subject's body.

13. The method of claim 12, (a) wherein the desired treatment location is in the left renal artery and wherein the method further comprises positioning a third ground pad of the plurality of ground pads on a left lateral side of the subject's body and/or (b) wherein the desired treatment location is in the right renal artery and wherein the method further comprises positioning a fourth ground pad of the plurality of ground pads on a right lateral side of the subject's body.

14. The method of claim 11, wherein the method is a method for performing intravascular renal nerve modulation and wherein method comprises positioning the first ground pad and a third ground pad of the plurality of ground pads on an anterior side of the subject's body, positioning the second ground pad and a fourth ground pad of the plurality of ground pads on a posterior side of the subject's body, and positioning a fifth ground pad of the plurality of ground pads on a lateral side of the subject's body.

15. The method of claim 11, wherein the method is a method for performing intravascular renal nerve modulation and wherein method comprises positioning the first ground pad and a third ground pad of the plurality of ground pads on an anterior side of an upper torso of the subject's body, positioning the second ground pad and a fourth ground pad of the plurality of ground pads on the anterior side of a lower torso of the subject's body, positioning a fifth ground pad and sixth ground pad of the plurality of ground pads on a posterior side of the upper torso of the subject's body, and positioning a seventh ground pad and an eight ground pad of the plurality of ground pads on the posterior side of the lower torso of the subject's body.

16. The method of claim 11, wherein the processor automatically modulates the resistance of at least one of the individual circuits such that each of the individual circuits has approximately the same impedance.

17. The method of claim 16, wherein the resistance of at least one of the individual circuits is automatically modulated both prior to and during intravascular nerve modulation.

18. The method of claim 16, wherein the resistance of at least one of the individual circuits is automatically modulated prior to, but not during, intravascular nerve modulation.

* * * * *